(12) United States Patent
Mertelmeier et al.

(10) Patent No.: US 10,271,806 B2
(45) Date of Patent: Apr. 30, 2019

(54) SUPPLEMENTARY SYSTEM FOR INTERFEROMETRIC X-RAY IMAGING AND PROJECTIVE X-RAY DEVICE

(71) Applicant: SIEMENS AKTIENGESELLSCHAFT, München (DE)

(72) Inventors: Thomas Mertelmeier, Erlangen (DE); Marcus Radicke, Veitsbronn (DE)

(73) Assignee: Siemens Healthcare GmbH, Erlangen (DE)

( * ) Notice: Subject to any disclaimer, the term of this patent is extended or adjusted under 35 U.S.C. 154(b) by 240 days.

(21) Appl. No.: 15/123,726

(22) PCT Filed: Feb. 24, 2015

(86) PCT No.: PCT/EP2015/053814
§ 371 (c)(1),
(2) Date: Sep. 6, 2016

(87) PCT Pub. No.: WO2015/132095
PCT Pub. Date: Sep. 11, 2015

(65) Prior Publication Data
US 2017/0014091 A1   Jan. 19, 2017

(30) Foreign Application Priority Data
Mar. 3, 2014 (DE) .......................... 10 2014 203 811

(51) Int. Cl.
*G03H 5/00* (2006.01)
*A61B 6/04* (2006.01)
(Continued)

(52) U.S. Cl.
CPC .......... *A61B 6/4291* (2013.01); *A61B 6/0414* (2013.01); *A61B 6/06* (2013.01);
(Continued)

(58) Field of Classification Search
CPC .......... A61B 6/0414; A61B 6/06; A61B 6/08; A61B 6/4291; A61B 6/4441; A61B 6/484;
(Continued)

(56) References Cited

U.S. PATENT DOCUMENTS 7,440,542 B2   10/2008   Baumann et al.
7,535,986 B2    5/2009   Hempel
(Continued)

FOREIGN PATENT DOCUMENTS

CN   101257851 A   9/2008
CN   101495853 A   7/2009
(Continued)

OTHER PUBLICATIONS

Pfeiffer, F., et al., "Phase retrieval and differential phase-contrast imaging with low-brilliance X-ray sources", Physics, 2006, pp. 1-4, vol. 2, Nature Publishing Group, URL: https://www.researchgate.net/publication/37452532_Phase_retrieval_and_differential_phase-contrast_imaging_with_low-brilliance_X-ray_sources.

*Primary Examiner* — Irakli Kiknadze
(74) *Attorney, Agent, or Firm* — Laurence Greenberg; Werner Stemer; Ralph Locher

(57) ABSTRACT

An X-ray device and a supplementary system are provided for interferometric X-ray imaging of a patient on the X-ray device in order to generate projective absorption recordings. An emitter-detector system includes a focus-forming X-ray tube and a digital flat-panel detector having a multiplicity of pixel-generating detector elements. A computer system has a program memory. A mobile grating attachment includes a first interferometric X-ray grating, a second interferometric X-ray grating disposed at a distance from the first X-ray grating in the radiation direction, and a displacement device for displacing the second X-ray grating in the plane of the (Continued)

second X-ray grating in steps over at least one detector element.

10 Claims, 3 Drawing Sheets

(51) Int. Cl.
  *A61B 6/00* (2006.01)
  *A61B 6/06* (2006.01)
  *A61B 6/08* (2006.01)

(52) U.S. Cl.
  CPC ............ *A61B 6/4441* (2013.01); *A61B 6/484* (2013.01); *A61B 6/502* (2013.01); *A61B 6/547* (2013.01); *A61B 6/08* (2013.01)

(58) Field of Classification Search
  CPC ....... A61B 6/502; A61B 6/547; A61B 6/4021; A61B 6/482; A61B 6/4208; A61B 6/00; A61B 6/4233; A61B 6/4007; A61B 6/505; A61B 6/5282; A61B 6/4035; A61B 6/5258; A61B 6/586; A61B 6/04; A61B 6/032; A61B 6/4452; A61B 6/4488; G01N 2223/076; G01N 23/223; G01N 2223/053; G01N 2223/419; G01N 2223/612; G01N 23/04; G01N 23/046; G01N 23/20; G01N 23/203; G01N 23/22; G01N 2223/314; G01N 2223/345
  USPC ...................................... 378/36, 37, 62, 98.8
  See application file for complete search history.

(56) References Cited

U.S. PATENT DOCUMENTS

| | | | |
|---|---|---|---|
| 2009/0092227 | A1 | 4/2009 | David et al. |
| 2009/0316857 | A1 | 12/2009 | David et al. |
| 2011/0293064 | A1 | 12/2011 | Huang et al. |
| 2012/0020454 | A1 | 1/2012 | Murakoshi |
| 2012/0153181 | A1 | 6/2012 | Iwakiri et al. |
| 2012/0195404 | A1 | 8/2012 | Omura |
| 2013/0129049 | A1 | 5/2013 | Ishii |
| 2013/0259194 | A1 | 10/2013 | Yip et al. |
| 2013/0308750 | A1* | 11/2013 | Ishii .................... A61B 6/4233 378/36 |
| 2014/0037059 | A1 | 2/2014 | Suft |
| 2014/0112440 | A1 | 4/2014 | David et al. |
| 2014/0185746 | A1 | 7/2014 | Baturin et al. |
| 2015/0071402 | A1* | 3/2015 | Handa .............. G01N 23/20075 378/36 |
| 2015/0092915 | A1* | 4/2015 | Anton .................. A61B 6/4283 378/36 |

FOREIGN PATENT DOCUMENTS

| | | |
|---|---|---|
| CN | 101943668 A | 1/2011 |
| CN | 102971620 A | 3/2013 |
| CN | 104869905 A | 8/2015 |
| DE | 102006015355 A1 | 8/2007 |
| DE | 102006015356 A1 | 8/2007 |
| DE | 102006015358 A1 | 8/2007 |
| DE | 102006046034 A1 | 8/2007 |
| JP | H08280656 A | 10/1996 |
| JP | 2009011488 A | 1/2009 |
| JP | 2011206280 A | 10/2011 |
| JP | 2012024339 A | 2/2012 |
| JP | 2012143550 A | 8/2012 |
| JP | 2012152466 A | 8/2012 |

* cited by examiner

SUPPLEMENTARY SYSTEM FOR INTERFEROMETRIC X-RAY IMAGING AND PROJECTIVE X-RAY DEVICE

BACKGROUND OF THE INVENTION

Field of the Invention

The invention relates to a supplementary system for interferometric x-ray imaging of a patient at an x-ray apparatus for generating projective absorption records comprising an emitter-detector system made of an x-ray tube which forms a focus and a digital flat-panel detector with a multiplicity of pixel-generating detector elements and a computer system comprising a program memory. Furthermore, the invention also relates to an x-ray device for generating projective absorption records using an emitter-detector system, which has the aforementioned supplementary system.

Interferometric x-ray imaging is based on the introduction of one, two or three gratings into the x-ray imaging system. Typically, the gratings are denoted G0, G1 and G2 in accordance with their sequence in the beam path. The absorption grating G0 is situated in the vicinity of the x-ray source and ensures that the coherence condition necessary for imaging is maintained, even in the case of relatively large x-ray foci. If the x-ray focus is very small, i.e. in the range <100 µm, an absorption grating is not required and it can be omitted. Usually, the absorption grating is constructed as a one-dimensional grating made of a multiplicity of grating lamellas, which are also referred to as grating webs, arranged in parallel such that the coherence condition is only satisfied in one direction. However, it can also have a checkerboard-like design and therefore meet the necessary coherence condition in both directions.

The distances between the grating lamellas are typically configured in such a way that the Laue effect is satisfied such that there is constructive superposition of the individual grating cutouts in the image plane.

By way of the first phase grating G1, the Talbot effect, which generates a self-image of the grating at specific distances from the grating G1, is used. The self-image of the grating G1 is interfered with by inserting the object to be measured into the beam path. From this interference, it is possible to obtain the image information relating to absorption, differential phase shift and dark field.

If use is made of a medical digital flat-panel detector, the resolution of this detector generally does not suffice to read out the interference pattern. This is why the introduction of a second grating G2 becomes necessary. In respect of the grating period thereof, this grating is matched to the non-interfered with self-image of the grating G1. The image information can be obtained by displacing one grating, typically the grating G2, and reading out both an image without an object and an image with an object. In principle, x-ray devices with correspondingly installed grating arrangements for generating interferometric x-ray images are known. By way of example, reference in this respect is made to the patent application DE 10 2006 015 355 A1 or the document Pfeiffer, Phase retrieval and differential phase-contrast imaging with low-brilliance X-ray sources, Nature Physics, 258-261, 2006.

A problem of the x-ray devices presented there consists of the fact that the design thereof is very cost-intensive as the production of x-ray optical gratings with the dimensions required there is very complicated and, currently, it is only possible to produce gratings with dimensions of 50 mm×50 mm. The modular assembly of a plurality of such gratings likewise harbors great problems.

BRIEF SUMMARY OF THE INVENTION

It is therefore an object of the invention to find a solution with which simple, already existing projective x-ray apparatuses can be used for generating interferometric x-ray images, at least using a smaller portion of the digital flat-panel detector used there.

This object is achieved by the features of the independent patent claims. Advantageous developments of the invention are the subject matter of dependent claims.

The inventors have identified that it is possible to equip available projective x-ray devices comprising a digital flat-panel detector with a supplementary system of at least two interferometric x-ray gratings and, using this, to carry out interferometric x-ray imaging. To this end, e.g. a mammography system, a thorax x-ray system or else a C-arm system can be supplemented with a corresponding mobile grating attachment. Here, according to the invention, the operating program of the x-ray device is also appropriately assisted by program supplements such that the computer of the x-ray device additionally serves to control the supplementary device and also assumes the evaluation of the image data in the case of the interferometric measurement. With the aid of the interferometric measurements which can be carried out by way of such a supplementary system, it is possible to generate both a differential phase image and a dark-field image in addition to normal absorption images. For evaluation purposes, at least two, or else all three, images can be merged or displayed next to one another in parallel. In accordance with the projective x-ray device used here, these interferometric x-ray images are likewise projective images.

Accordingly, the inventors propose a supplementary system for interferometric x-ray imaging of a patient at an x-ray apparatus for generating projective absorption records comprising an emitter-detector system made of an x-ray tube which forms a focus and a digital flat-panel detector with a multiplicity of pixel-generating detector elements and a computer system comprising a program memory, comprising:

a mobile grating attachment, comprising:
a first interferometric x-ray grating,
a second interferometric x-ray grating arranged at a distance from the first x-ray grating in the radiation direction, and
a displacement device for displacing the second x-ray grating in steps in the plane of the second x-ray grating over at least one detector element,
and a computer program to be stored and executed in the computer system, which computer program controls the supplementary device and creates at least one interferometric x-ray image.

In principle, it is possible to realize projective interferometric imaging with the above-described supplementary system if the focus used in the x-ray apparatus is small enough to satisfy the necessary coherence conditions. However, if the focus of the employed x-ray tube is too large, it is possible to attach a grating front attachment to an absorption grating to the x-ray tube in order to satisfy the coherence conditions in at least one direction in the case of a lamella-type design of the grating. Alternatively, it is also possible to select a checkerboard-like design such that the coherence conditions are satisfied in both directions. This measure also renders it possible to employ x-ray tubes which produce a sufficiently high dose power so that measurement times which are too long do not become necessary for interferometric imaging.

When using an absorption grating, it can be advantageous if the absorption grating is movably arranged in the grating front attachment. By way of example, this grating can then be pushed or tilted into the beam path for an interferometric examination, while it is removed from the beam path during the regular absorption recording.

Furthermore, the supplementary system can be configured in such a way that the grating attachment with the two interferometric gratings is embodied for direct attachment onto the flat-panel detector. In most cases, the flat-panel detector is placed relatively close to the patient in the case of projective absorption imaging. However, since the grating attachment has a non-negligible installation height on account of the necessary distance between the two interferometric gratings, a corresponding distance must be maintained between the flat-panel detector and the patient when using the supplementary system in order to be able to place the grating attachment between said flat-panel detector and patient. On account of the divergence of the beam path used for the examination, a magnification of the region examined with the grating attachment accordingly also arises which, for example, typically lies in the region of a magnification factor of 1.3-times to 2-times in the case of a mammography examination.

In most cases, the supplementary system according to the invention will be configured in such a way that the grating attachment on the flat-panel detector only covers a portion of the flat-panel detector. Accordingly, it is necessary to determine the position of the grating attachment. To this end, provision can be made according to the invention of a position detection system which, in an exemplary manner, is attached to the grating attachment and/or to the flat-panel detector, and a position representation system should be present such that the region covered by the supplementary system is indicated directly on the patient or on an image representation thereof. In so doing, coupling arises between the grating attachment attached to the flat-panel detector and a position indication of the interferometrically scanned region on the patient. As an alternative to the display on the patient, or in addition thereto, it is also possible to indicate on a monitor the region covered by the grating attachment in a photographic image record or in a previously generated absorption x-ray record of the patient in accordance with the positioning of the grating attachment on the flat-panel detector. As a result, the operating staff can easily undertake the desired positioning of the interferometric gratings.

Accordingly, the position detection system can have position sensors, which are integrated into the flat-panel detector and detect position encoders in the grating attachment. Furthermore, a device for generating light marks can be attached in the region of the x-ray tube, said device projecting the position of the grating attachment onto the examination object.

In a further variant, the computer program can also emulate a method, by means of which a region of particular interest is characterized in a previously recorded projection x-ray absorption image of the examination object and this region is depicted on the flat-panel detector by a device for generating light marks such that the grating attachment for generating at least one interferometric x-ray image of this region can be positioned, wherein the at least one interferometric x-ray image can be a phase image and/or a differential phase image and/or a dark-field image and/or absorption image, which is obtained from the interferometric measurement data. Reference is made to the fact that the scope of the invention also includes combinations, possibly weighted combinations, of the aforementioned images under the term interferometric x-ray imaging. Here, the weighting can both take place automatically and be influenced by manual adjustment of at least one weighting factor.

In addition to the above-described supplementary device, the inventors also propose an x-ray device, which is embodied for projective absorption imaging and comprises an emitter-detector system made of an x-ray tube which forms a focus and a digital flat-panel detector with a multiplicity of pixel-generating detector elements and a computer system comprising a program memory, wherein the x-ray device has a supplementary system according to the invention for additionally generating at least one of the aforementioned interferometric x-ray images.

In particular, it is proposed to combine the supplementary system with a mammography system, a C-arm system or a thorax x-ray apparatus with a wall stand.

What is advantageous here, in particular, is if this x-ray device has on the flat-panel detector thereof an automatic positioning device for the grating attachment, which is embodied in such a way that it positions the grating attachment in accordance with preceding inputs on a previously recorded absorption record. Here, appropriate routines are present in the supplementary computer software, said routines carrying out the automatic positioning of the grating attachment.

BRIEF DESCRIPTION OF THE SEVERAL VIEWS OF THE DRAWING

Below, the invention will be explained in more detail on the basis of preferred exemplary embodiments with the aid of the figures, with only the features required for understanding the invention being depicted. Use is made of the following reference signs: 1: x-ray device; 2: flat-panel detector; 2.1: detector elements; 3: grating attachment; 4: compression plate; 5: compression plate; 6: examination object; 6.1: patient; 7: focus; 7.1: x-ray tube; 7.2: recording and display system; 8: grating front attachment; 9: region of particular interest; 10: beam cone; 10.1: restricted beam cone; 11: computer/computer system; 12: displacement device; 13: displaceable stops; 14: sensors/actuators; 15: portion; G0: absorption grating; G1: first interferometric grating; G2: second interferometric grating; $Prg_1$-$Prg_N$: computer programs.

In detail.

DESCRIPTION OF THE INVENTION

Figure 1:
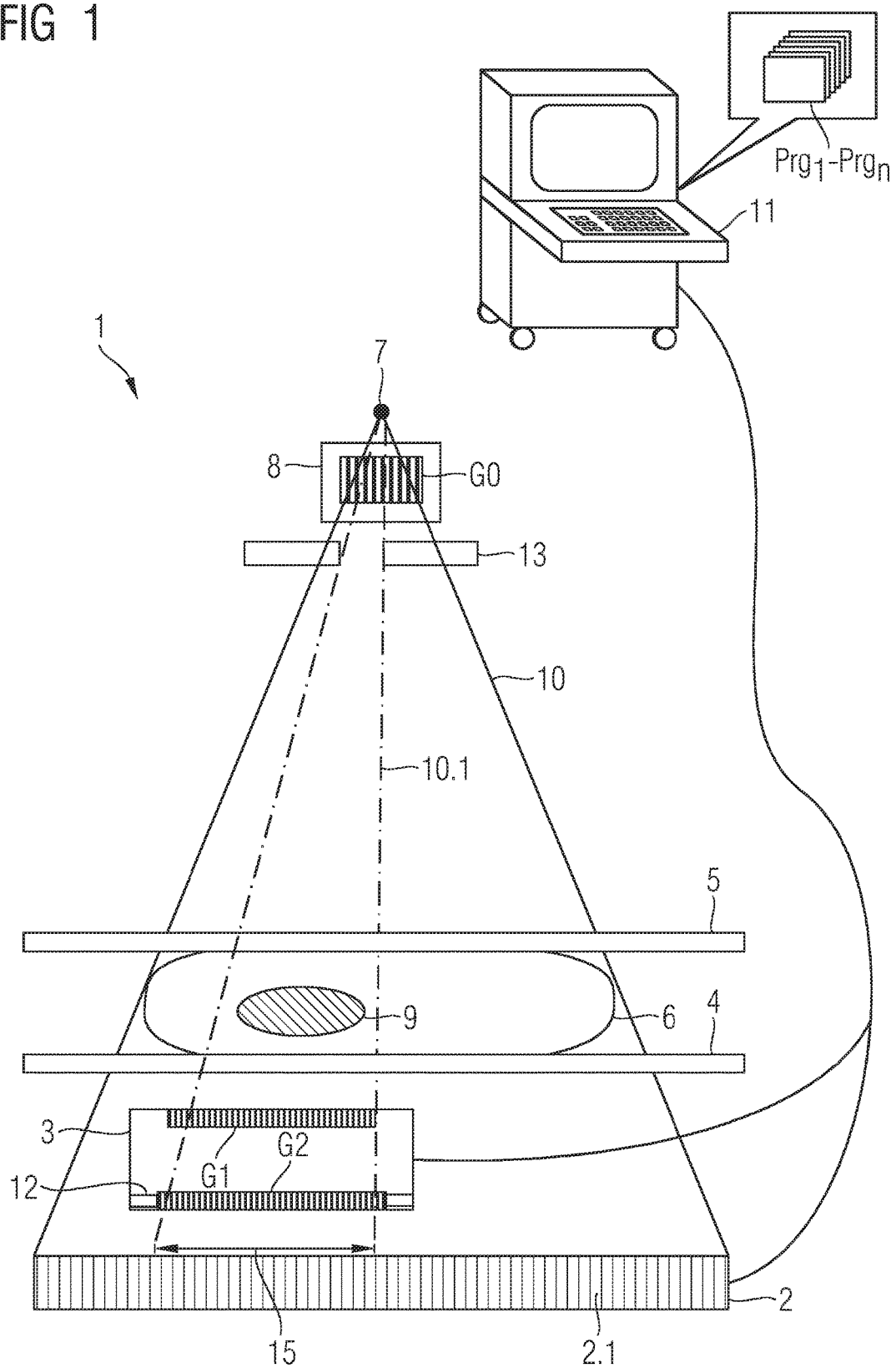
FIG. 1 shows a schematic illustration of a mammography system with a supplementary system for interferometric x-ray imaging.

A mammography system 1 is shown schematically in FIG. 1 in a first embodiment variant, in which mammography system a beam cone 10, which is directed onto an electronic flat-panel detector 2, is generated with the aid of a focus 7 at an x-ray tube (not depicted in any more detail here). The flat-panel detector 2 comprises a multiplicity of detector elements 2.1, which are arranged in a plane such that each detector element 2.1 generates a pixel of an x-ray image for reproducing an image. Arranged on the x-ray tube downstream of the focus 7 in the beam path there is a grating front attachment 8 with the absorption grating G0, which generates a multiplicity of very narrow x-ray sources with the aid of many grating webs or grating lamellas arranged in parallel and which hence meets the coherence condition for the interferometric examination. The examination object, the breast 6 of a female patient, is situated between two compression plates 4 and 5, as is conventional during a mammographic x-ray recording. On account of preceding x-ray absorption imaging, a region 9 of particular interest was found, said region being intended to be examined in more detail with the interferometric examination shown here. Accordingly, the mobile grating attachment 3 was introduced into the beam path between breast and flat-panel detector 2. The region of the breast to be examined therewith corresponds to the portion 15 on the flat-panel detector 2 onto which the grating attachment 3 is projected. The correspondingly restricted beam cone 10.1 is depicted using a dash-dotted line. Situated in the grating attachment 3 there are in succession in the beam direction, and arranged in a plane parallel manner, the first interferometric grating G1 and the second interferometric grating G2 arranged at a distance therefrom. In the present exemplary embodiment, the second grating G2 is connected to a displacement device 12 in the form of an actuator or a plurality of actuators, by means of which the grating can be displaced step-by-step prior to each measurement in order to obtain the phase information of the x-ray radiation in a manner known per se from the absorption values of the downstream detector elements.

In principle, it is proposed to arrange the two gratings G1 and G2 at a predetermined fixed distance from one another, which is matched to the x-ray energy used in the examination. However, the scope of the invention also includes a variant of a mobile grating attachment, which additionally provides an adjustment device for an adjustable distance between the gratings G1 and G2 so that an adaptation to different x-ray energies is possible.

Since good quality gratings can currently only be produced up to dimensions of approximately 50 mm×50 mm and since the assembly of a plurality of modular individual gratings to form a large grating with a high quality is only achievable with much outlay, the portion on the flat-panel detector covered by a grating attachment will preferably also be of this order of magnitude. Since, furthermore, a relatively high dose power must be used for the interferometric measurement, this exemplary embodiment additionally also describes an optional stop system with a plurality of individually displaceable stops 13, which are preferably set automatically on the basis of the undertaken positioning of the grating attachment 3 or already on the basis of a region of particular interest 9 defined on the monitor.

In principle, a so-called magnification table is known per se from mammography, with the breast being mounted on said magnification table and being compressed from above by means of a compression plate. When using this magnification table, the upper detector cover can be replaced by the magnification table in order to keep the attenuation of the image signal by additional absorbers as low as possible. According to the invention, the grating attachment 3 can be used with such a magnification table and inserted between detector and compression plate of the magnification table. Alternatively, the grating attachment can also be integrated into such a variably attachable magnification table, wherein an automatic positioning device for the grating attachment 3 can preferably also be attached in that case.

In the present exemplary embodiment, the grating attachment 3 is connected to the computer 11 via a wired connection such that said computer can also control the supplementary device in addition to controlling the mammography system with the aid of the programs $Prg_1$-$Prg_n$ carried out and stored therein. However, in principle, it is also within the scope of the invention if such linking of the supplementary device is brought about wirelessly, for example by way of a secure Bluetooth or WLAN connection. Naturally, the conventional transmitters and receivers must be present in the supplementary system, in particular in the grating attachment 3, and in the computer 11 for this purpose.

As a result of the mammography system explained herein with the additional supplement for interferometric examinations, improved differential diagnostics are rendered possible in a cost-effective manner by way of additional interferometric image information, for example in the form of phase-contrast records or dark-field records, for selected portions of the patient. Here, the proposed supplementary system can easily be used with already available mammography systems.

Figure 2:
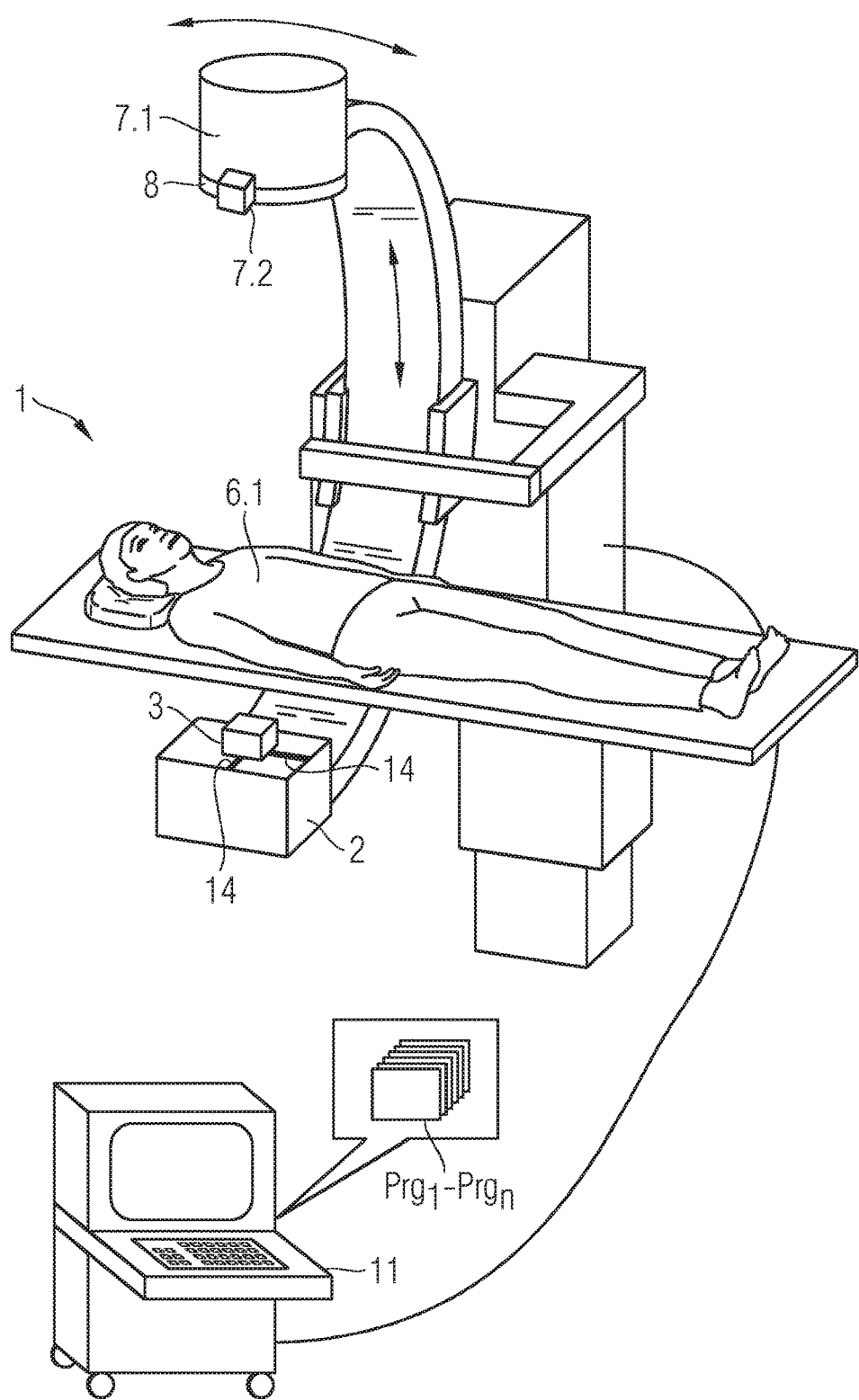
FIG. 2 shows a schematic illustration of a C-arm system with a supplementary system for interferometric x-ray imaging.

In another application of the supplementary system, the latter can also be used in conjunction with a C-arm system 1 known per se, as is shown in an exemplary manner in FIG. 2. The C-arm system 1 comprises an emitter-detector system consisting of an x-ray tube 7.1 and an opposing digital flat-panel detector 2, said emitter-detector system being arranged in a movable manner at a C-arm. Arranged at the x-ray tube 7.1 is a grating front attachment 8, in which there is an absorption grating G0 which can be fixed in front where necessary. Moreover, a light-based recording and display system 7.2 is attached to the x-ray tube, the former enabling the patient 6.1 lying on the patient couch to be displayed on the monitor of the computer 11 and enabling light markings to be generated on the patient 6.1. According to the invention, a grating attachment 3 is furthermore attached onto the flat-panel detector 2, with both interferometric gratings G1 and G2 being situated in said grating attachment. Furthermore, two sensors and/or actuators 14 for the grating attachment 3 are attached to the detector 2 such that, firstly, the position of the grating attachment 3 can be detected and/or actuated by control by way of the computer 11. In accordance with an optionally manual or semi-manual positioning of the grating attachment 3, it is then possible to indicate the projected position of the grating attachment 3 on the patient 6.1 with the aid of the recording and display system 7.2. Alternatively, the desired position of the grating attachment 3 can also be determined by the operating staff or automatically by a corresponding marking on an image or x-ray image of the patient 6.1 on the computer 11 such that the system thereupon undertakes the correct positioning of the grating attachment 3. In accordance with the positioning of the grating attachment 3, the beam emanating from the x-ray tube can also be restricted to the portion of the detector 2 to be examined interferometrically with the aid of controllable stops.

In addition to this, it should be noted that it may be advantageous to fasten the grating attachment 3 not on the relatively delicate C-arm but rather directly on the suspension device of the C-arm or directly on the ceiling or floor of the examination chamber. On account of the lower weight in comparison with the C-arm, it is possible to set far more stable positioning and this can be maintained better over time. Hence, the grating front attachment 3 with the gratings G1 and G2 can be moved parallel to the C-arm, but it is decoupled therefrom in terms of vibrations. This is therefore advantageous because the effects of vibrations or relative motion depends strongly on the objects between which the relative motion occurs. The greatest amount of stability is required between the gratings G1 and G2, as the image quality in this case can already be influenced negatively by relative movements of a few micrometers. By contrast, relative movements between tube and detector can be one to two orders of magnitude higher without strongly influencing the image quality.

Figure 3:
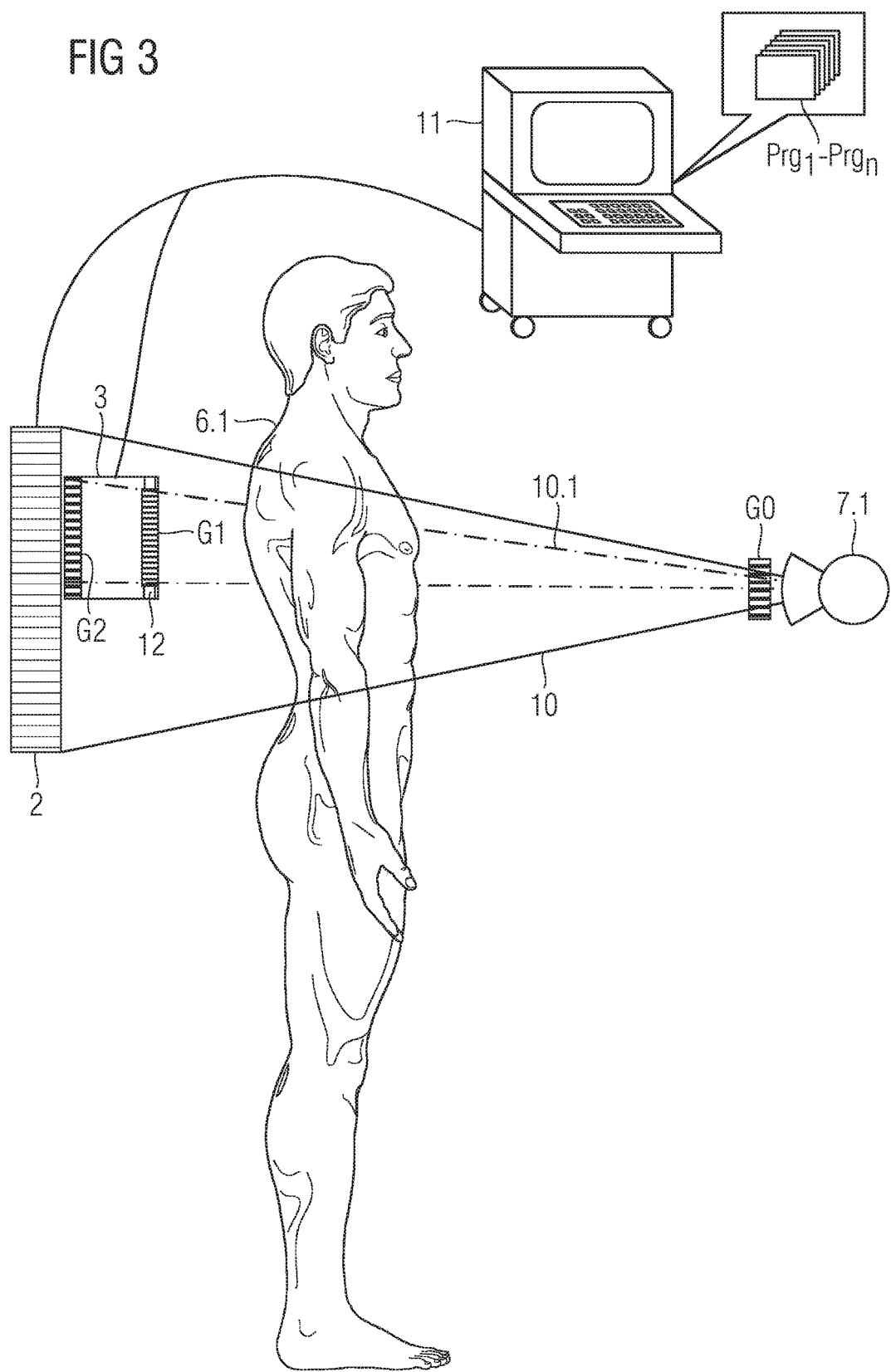
FIG. 3 shows a schematic illustration of a thorax x-ray device with a supplementary system for interferometric x-ray imaging

A further application possibility of the supplementary system according to the invention is described using FIG. 3, which schematically shows a thorax x-ray device 1. In the art, such thorax x-ray devices are also referred to as Bucky wall stands. It comprises an x-ray tube 7.1 fastened to a displaceable frame, from which x-ray tube a beam cone 10—generally with a horizontal alignment—is aligned onto an opposite flat-panel detector 2. By way of a mechanism not depicted in any more detail here, the flat-panel detector 2 is coupled to the x-ray tube 7.1 in this case in such a way that the flat-panel detector 2 always moves together with the vertical movements of the x-ray tube 7.1, while free horizontal movement of the x-ray tube 7.1 is possible. In the case of such a movement, all that is changed is the widening of the beam cone 10 with the aid of adjustable stops, so that no unnecessary beam dose is administered away from the detector.

According to the invention, a grating attachment 3 which enables an interferometric examination for a portion 15 of the flat-panel detector 2 is situated upstream of the detector 2. Here, the two gratings G1 and G2 can be securely installed at the required distance, they can be inserted at different predetermined distances or else an automatic adjustment device may be present, which automatically sets the spacing between the gratings. This device is constructed in such a way that the gratings G1 and G2 are aligned with respect to one another with high precision. Moreover, automatic repositioning of the gratings G1 and G2 can be carried out by way of an automatic measurement of the path between focus or absorption grating and detector such that the distance conditions required for the interferometric examination are maintained.

Once again, the two gratings G1 and G2 are housed in the grating attachment 3, with the grating G1 being arranged in a displaceable manner in this case. Slightly more space is available for the displacement device 12 due to the divergence of the x-ray beam cone 10 or the restricted x-ray beam cone 10.1.

In principle, an automatic positioning device and/or a position determination device for the grating attachment 3 and/or a light-based recording and/or display system can also be used in front of the patient 6.1 in this case so as to carry out the positioning of the grating attachment 3 in a manual, semiautomatic or fully automatic manner, as desired.

The interferometric examination itself is then carried out using additional computer programs $Prg_1$-$Prg_n$ installed on the computer 11. As a result, this also allows phase-contrast records and dark-field records of selected portions to be generated, which can be depicted on their own or in weighted combinations, or else in combination with absorption records.

In particular, the supplementary system described here can also be used in conjunction with mobile detectors, which can be inserted in a known fashion into the Bucky wall stand.

Even though the invention was described and illustrated more closely in detail by the preferred exemplary embodiment, the invention is not restricted by the disclosed examples and other variations can be derived herefrom by a person skilled in the art without departing from the scope of protection of the invention.

LIST OF REFERENCE SIGNS

1 X-ray device
2 Flat-panel detector
2.1 Detector elements
3 Grating attachment
4 Compression plate
5 Compression plate
6 Examination object
6.1 Patient
7 Focus
7.1 X-ray tube
7.2 Recording and display system
8 Grating front attachment
9 Region of particular interest
10 Beam cone
10.1 Restricted beam cone
11 Computer/computer system
12 Displacement device
13 Displaceable stops
14 Sensors/actuators
15 Portion
G0 Absorption grating
G1 First interferometric grating
G2 Second interferometric grating
$Prg_1$-$Prg_N$ Computer programs

The invention claimed is:

1. In an x-ray apparatus for generating projective absorption records, including an emitter-detector system having an x-ray tube forming a focus and defining a radiation direction and a digital flat-panel detector with a multiplicity of pixel-generating detector elements, and a computer system having a program memory, a supplementary system for interferometric x-ray imaging of a patient at the x-ray apparatus, the supplementary system comprising:
 a mobile grating attachment including:
  a first interferometric x-ray grating,
  a second interferometric x-ray grating disposed at a distance from said first x-ray grating in the radiation direction and defining a plane of said second x-ray grating, and
  a displacement device for displacing said second x-ray grating in steps in said plane of said second x-ray grating over at least one of the detector elements;
 a position detection system attached to at least one of said mobile grating attachment or said flat-panel detector;
 a position representation system for indicating a region covered by the supplementary system directly on a patient or on an image representation of a Patient; and
 a non-transitory computer program to be stored and executed in the computer system for controlling the supplementary system and creating at least one interferometric x-ray image.

2. The supplementary system according to claim 1, which further comprises a grating front attachment having an absorption grating and being attached to said x-ray tube.

3. The supplementary system according to claim 2, which further comprises an absorption grating being movably disposed in said grating front attachment.

4. The supplementary system according to claim 1, wherein said mobile grating attachment is configured for direct attachment to said flat-panel detector.

5. The supplementary system according to claim 1, wherein said position detection system has position sensors integrated into said flat-panel detector and position encoders in said mobile grating attachment.

6. The supplementary system according to claim 1, which further comprises a device attached in a vicinity of said x-ray tube for generating light marks, said light marks projecting the position of said mobile grating attachment onto an examination object.

7. The supplementary system according to claim 1, wherein:
   said computer program is executed by said computer to perform a method for marking a region of particular interest in a previously recorded projective x-ray absorption image of the patient; and
   a device for generating light marks depicts the region on said flat-panel detector, permitting said mobile grating attachment to be positioned for generating at least one interferometric x-ray image representation of the region selected from the group consisting of a phase image, a differential phase image, a dark-field image and an absorption image.

8. An x-ray device for projective absorption imaging, the x-ray device comprising:
   an emitter-detector system including an x-ray tube forming a focus and a digital flat-panel detector having a multiplicity of pixel-generating detector elements;
   a computer system including a program memory; and
   a supplementary system according to claim 1 for additionally generating at least one interferometric x-ray image representation selected from the group consisting of a phase image, a differential phase image, a dark-field image and an absorption image.

9. The x-ray device according to claim 8, wherein the x-ray device is a mammography system, a C-arm system or a thorax x-ray apparatus with a wall stand.

10. An x-ray device for projective absorption imaging, the x-ray device comprising:
   an emitter-detector system including an x-ray tube forming a focus and a digital flat-panel detector having a multiplicity of pixel-generating detector elements;
   a computer system including a program memory;
   a supplementary system for additionally generating at least one interferometric x-ray image representation selected from the group consisting of a phase image, a differential phase image, a dark-field image and an absorption image, said supplementary system having a mobile grating attachment including:
      a first interferometric x-ray grating,
      a second interferometric x-ray grating disposed at a distance from said first x-ray grating in the radiation direction and defining a plane of said second x-ray grating, and
      a displacement device for displacing said second x-ray grating in steps in said plane of said second x-ray grating over at least one of the detector elements;
   a non-transitory computer program to be stored and executed in the computer system for controlling said supplementary system and creating at least one interferometric x-ray image; and
   an automatic positioning device attached to said flat-panel detector for positioning said mobile grating attachment, said positioning device positioning said mobile grating attachment in accordance with preceding entries on a previously recorded absorption record.

* * * * *